United States Patent
Bitto et al.

(10) Patent No.: US 9,989,391 B2
(45) Date of Patent: Jun. 5, 2018

(54) COIL

(71) Applicant: Endress + Hauser Flowtec AG, Reinach (CH)

(72) Inventors: Ennio Bitto, Aesch (CH); Gerhard Eckert, Grenzach-Wyhlen (DE)

(73) Assignee: Endress + Hauser Flowtec AG, Reinach (CH)

( * ) Notice: Subject to any disclaimer, the term of this patent is extended or adjusted under 35 U.S.C. 154(b) by 40 days.

(21) Appl. No.: 15/104,001

(22) PCT Filed: Nov. 17, 2014

(86) PCT No.: PCT/EP2014/074712
§ 371 (c)(1),
(2) Date: Jun. 13, 2016

(87) PCT Pub. No.: WO2015/090776
PCT Pub. Date: Jun. 25, 2015

(65) Prior Publication Data
US 2016/0313162 A1  Oct. 27, 2016

(30) Foreign Application Priority Data

Dec. 20, 2013 (DE) .......... 10 2013 114 731
Mar. 25, 2014 (DE) .......... 10 2014 104 095

(51) Int. Cl.
*G01F 1/84* (2006.01)
*G01N 9/00* (2006.01)
(Continued)

(52) U.S. Cl.
CPC .......... *G01F 1/8422* (2013.01); *G01F 1/8409* (2013.01); *G01N 9/002* (2013.01);
(Continued)

(58) Field of Classification Search
CPC ........................................................ G01F 1/84
See application file for complete search history.

(56) References Cited

U.S. PATENT DOCUMENTS 3,949,606 A * 4/1976 Blancett ............... G01F 1/0755
73/258
4,122,425 A   10/1978 Hughes
(Continued)

FOREIGN PATENT DOCUMENTS

DE 1935366 A1 2/1970
DE 3232533 A1 5/1983
(Continued)

OTHER PUBLICATIONS

English Translation of International Preliminary Report on Patentability, WIPO, Geneva, dated Jun. 30, 2016.
(Continued)

*Primary Examiner* — Jewel V Dowtin
(74) *Attorney, Agent, or Firm* — Bacon & Thomas, PLLC

(57) ABSTRACT

The coil (1) comprises a platform (11) having a passageway (11A; 11A) extending from an end (11+) of the platform formed by a first end face to an end (11#) of the platform distal to the end (11+) and formed by a second end face, and a coil support (12) having a passageway (12A) extending from an end (12+) of the coil support formed by a first end face to an end (12#) of the coil support distal to the first end and formed by a second end face. The coil support (12) is so arranged relative to the platform (11) that the second end face of the coil support faces the platform and an intermediate space (20) is formed between the second end face of the coil support and the first end face of the platform, and that the passageway (12A) of the coil support aligns with the passageway (11A) of the platform. The coil (1) additionally comprises a screw (13) accommodated both by the passageway of the coil support as well as also by the passageway of (Continued)

the platform for the mechanical connecting of coil support and platform, a coil wire (14) of an electrically conductive material wound around the coil support, as well as at least two connecting lines (111, 112), in each case, placed partially in the intermediate space formed between coil support and platform, of which connecting lines a connecting line (111) has at least one conductor (111A) of electrically conductive material electrically conductively connected with an end (14+) of the coil wire and a connecting line (112) has at least one conductor (112A) of electrically conductive material electrically conductively connected with an end (14#) of the coil wire. The coil is provided especially also for application in a measuring transducer of vibration-type.

51 Claims, 10 Drawing Sheets

(51) Int. Cl.
| | | |
|---|---|---|
| *G01N 11/16* | (2006.01) | |
| *H01F 5/04* | (2006.01) | |
| *H01F 5/02* | (2006.01) | |
| *H01F 27/06* | (2006.01) | |

(52) U.S. Cl.
CPC ............... *G01N 11/16* (2013.01); *H01F 5/02* (2013.01); *H01F 5/04* (2013.01); *H01F 27/06* (2013.01)

(56) References Cited

U.S. PATENT DOCUMENTS

| | | |
|---|---|---|
| 4,601,765 A | 7/1986 | Soileau et al. |
| 4,904,974 A | 2/1990 | Tsuji |
| 5,429,002 A | 7/1995 | Colman |
| 6,362,717 B1 | 3/2002 | Lewin |
| 8,096,192 B2 | 1/2012 | Shimizu et al. |
| 8,201,460 B2 | 6/2012 | Bitto et al. |
| 9,068,868 B2 * | 6/2015 | Voigt .................. G01F 1/584 |

FOREIGN PATENT DOCUMENTS

| | | |
|---|---|---|
| DE | 3629006 A1 | 3/1988 |
| DE | 102009032247 A1 | 6/2010 |
| DE | 102013114731 A1 | 6/2015 |
| FR | 2172901 A1 | 10/1973 |
| GB | 962090 A | 6/1964 |
| GB | 2108769 A | 5/1983 |
| JP | S6129106 A | 2/1986 |
| JP | H02177514 A | 7/1990 |

OTHER PUBLICATIONS

International Search Report EPO, The Netherlands, dated Jan. 30, 2015.
German Search Report, German PTO, Munich, dated Jan. 27, 2014.

* cited by examiner

COIL

TECHNICAL FIELD

The invention relates to a coil, especially a coil for application in a measuring transducer of vibration-type, not least of all also a coil suitable for forming an oscillation exciter and/or an oscillation sensor. Furthermore, the invention relates to a measuring transducer of vibration-type having such a coil.

BACKGROUND DISCUSSION

Vibronic measuring devices are used in industrial measurements technology, especially also in connection with the control and monitoring of automated manufacturing processes, for highly accurate ascertaining of one or more measured variables, especially a mass flow rate, a density and/or a viscosity of a medium, for example, a liquid or a gas, flowing in a process line, for example, a pipeline. Vibronic measuring devices are often formed by means of a measuring device electronics (which is most often formed by means of at least one microprocessor) as well as a measuring transducer of vibration-type electrically connected with the measuring device electronics and flowed-through during operation by the medium to be measured. Such measuring devices, for example, embodied as so-called four conductor—or also so-called two conductor devices, have been known for a long time, not least of all also in the form of Coriolis mass flow, density measuring devices or also in the form of viscosity, density measuring devices, and are established in industrial use. Examples of such vibronic measuring devices, respectively suitable measuring transducers, are described in, among other things, US-A 2006/0081069, US-A 2004/0123645, US-A 2006/0096390, US-A 2007/0062309, US-A 2007/0119264, US-A 2008/0047362, US-A 2008/0190195, US-A 2008/0250871, US-A 2010/0005887, US-A 2010/0011882, US-A 2010/0257943, US-A 2011/0161017, US-A 2011/0219872, US-A 2011/0265580, US-A 2012/0123705, US-A 2013/0042700, U.S. Pat. No. 4,491,009, U.S. Pat. No. 4,524,610, U.S. Pat. No. 4,756,198, U.S. Pat. No. 4,777,833, U.S. Pat. No. 4,801,897, U.S. Pat. No. 4,876,898, U.S. Pat. No. 4,996,871, U.S. Pat. No. 5,287,754, U.S. Pat. No. 5,291,792, U.S. Pat. No. 5,349,872, U.S. Pat. No. 5,531,126, U.S. Pat. No. 5,705,754, U.S. Pat. No. 5,796,010, U.S. Pat. No. 5,796,011, U.S. Pat. No. 5,831,178, U.S. Pat. No. 5,945,609, U.S. Pat. No. 5,965,824, U.S. Pat. No. 6,006,609, U.S. Pat. No. 6,092,429, U.S. Pat. No. 6,223,605, U.S. Pat. No. 6,311,136, U.S. Pat. No. 6,477,901, U.S. Pat. No. 6,513,393, U.S. Pat. No. 6,651,513, U.S. Pat. No. 6,666,098, U.S. Pat. No. 6,711,958, U.S. Pat. No. 6,840,109, U.S. Pat. No. 6,920,798, U.S. Pat. No. 7,017,424, U.S. Pat. No. 7,077,014, U.S. Pat. No. 7,200,503, U.S. Pat. No. 7,216,549, U.S. Pat. No. 7,325,462, U.S. Pat. No. 7,360,451, U.S. Pat. No. 7,792,646, WO-A 00/34748, WO-A 01/02 816, WO-A 2007/043996, WO-A 2008/059262, WO-A 2013/092104, WO-A 85/05677, WO-A 88/02853, WO-A 89/00679, WO-A 94/21999, WO-A 95/03528, WO-A 95/16897, WO-A 95/29385, WO-A 98/02725, and WO-A 99/40 394.

Measuring transducers of the measuring devices shown therein comprise at least one at least sectionally straight and/or at least sectionally curved, e.g. U-, V-, S-, Z- or Ω shaped, measuring tube having a lumen surrounded by a tube wall for guiding the medium.

The at least one measuring tube of such measuring transducers is adapted to guide medium in the lumen and concurrently to be so caused to vibrate that it executes wanted oscillations, namely mechanical oscillations, about a resting position with a wanted frequency also co-determined by the density of the medium and consequently usable as a measure for the density. In the case of conventional vibronic measuring devices, typically, bending oscillations at a natural resonant frequency serve as wanted oscillations, for example, such bending oscillations, which correspond to a measuring transducer inherent, natural bending oscillation, fundamental mode, in which the oscillations of the measuring tube are resonant oscillations, which have exactly one oscillatory antinode. The wanted oscillations are in the case of an at least sectionally curved measuring tube additionally typically so embodied that the measuring tube moves about an imaginary oscillation axis imaginarily connecting an inlet-side and an outlet-side end of the measuring tube in a pendulum-like manner as a kind of end clamped cantilever, while, in contrast, in the case of measuring transducers with a straight measuring tube the wanted oscillations are most often bending oscillations in a single imaginary plane of oscillation. It is additionally known for the purpose of performing repeated reviews of the measuring transducer during operation of the measuring device to excite the at least one measuring tube, at times, also for temporarily lasting times, to execute oscillations outside of resonance as well as to evaluate the oscillations outside of resonance, for example, in order, such as described in US-A 2012/0123705, to detect possible damage to the at least one measuring tube as early as possible, damage which can bring about an undesired lessening of the accuracy of measurement and/or the operational safety of the respective measuring device. In the case of measuring transducers with two measuring tubes, these are most often integrated into the particular process line via a distributor piece extending on the inlet side between the measuring tubes and an inlet-side connecting flange as well as via a distributor piece extending on the outlet side between the measuring tubes and an outlet-side connecting flange. In the case of measuring transducers with a single measuring tube, the latter communicates with the process line most often via a connecting tube opening on the inlet side as well as via a connecting tube opening on the outlet side. Furthermore, measuring transducers with a single measuring tube additionally comprise at least one counteroscillator of one or a plurality of parts. The counteroscillator is embodied, for example, to be tube-, box- or plate-shaped and is coupled to the measuring tube at a first coupling zone on the inlet side and to the measuring tube at a second coupling zone on the outlet side. During operation, the counteroscillator essentially rests or oscillates oppositely to the measuring tube. The inner part of the measuring transducer formed by means of measuring tube and counteroscillator is most often held alone by means of the two connecting tubes, via which the measuring tube communicates with the process line during operation, in a protective measuring transducer housing, especially in a manner enabling oscillations of the inner part relative to the measuring transducer housing. In the case of the measuring transducers shown, for example, in U.S. Pat. No. 5,291,792, U.S. Pat. No. 5,796,010, U.S. Pat. No. 5,945,609, U.S. Pat. No. 7,077,014, US-A 2007/0119264, WO-A 01/02 816 and WO-A 99/40 394 with a single, essentially straight, measuring tube, the latter and the counteroscillator are, such as quite usual in the case of conventional measuring transducers, essentially coaxially oriented relative to one another. Thus, the counteroscillator is embodied as an essentially straight hollow cylinder and so arranged in the measuring transducer that the measuring tube is at least partially jacketed by the counteroscillator. Materials used for such counteroscillators, especially also in the case of application of titanium, tantalum or zirconium for the measuring tube, are most often comparatively cost effective steel types, such as, for instance, structural steel or free-machining steel.

For active exciting, respectively maintaining, of oscillations of the at least one measuring tube, not least of all also the wanted oscillations, measuring transducers of vibration-type have, additionally, at least one electromechanical oscillation exciter acting during operation differentially on the at least one measuring tube and the, in given cases, present counteroscillator, respectively the, in given cases, present, other measuring tube. The oscillation exciter is electrically connected with the measuring device electronics by means of a pair of electrical connecting lines, for example, in the form of connection wires and/or in the form of conductive traces of a flexible circuit board, and serves, especially, operated by an electrical exciter signal generated by the measuring device electronics and correspondingly conditioned, namely at least per se matched to changing oscillation characteristics of the at least one measuring tube, to convert an electrical excitation power fed by means of the exciter signal into a drive force acting at a point of engagement on the at least one measuring tube formed by the oscillation exciter.

Oscillation exciters of usually marketed measuring transducers of vibration-type are typically constructed as a kind of oscillation coil working according to the electrodynamic principle, namely formed by means of a coil—in the case of measuring transducers with a measuring tube and a counteroscillator coupled thereto, most often affixed to the latter—as well as, serving as armature interacting with the at least one coil, a permanent magnet, which is affixed correspondingly to the measuring tube to be moved. The permanent magnet and the coil are, in such case, usually so oriented that they extend essentially coaxially to one another. Additionally, in the case of conventional measuring transducers, the oscillation exciter is most often so embodied and placed that it acts essentially centrally on the at least one measuring tube. Alternatively to an oscillation exciter acting rather centrally and directly on the measuring tube, it is possible, such as disclosed, among others, in the above cited U.S. Pat. No. 6,092,429, for example, also to use exciter mechanisms formed by means of two oscillation exciters affixed not in the center of the measuring tube, but, instead, rather on the inlet—, respectively on the outlet side thereof for the active exciting of mechanical oscillations of the at least one measuring tube or, such as, among other things, provided in U.S. Pat. No. 6,223,605 or U.S. Pat. No. 5,531,126, for example, also formed by means of an oscillation exciter acting between the, in given cases, present counteroscillator and the measuring transducer housing.

For registering oscillatory movements of the at least one measuring tube, not least of all also those corresponding to the wanted oscillations, measuring transducer of the type being discussed have, furthermore, mounted on the measuring tube, for example, electrically connected with the measuring device electronics by means of a pair of electrical connecting lines, at least one oscillation sensor, which is adapted to convert the oscillatory movements into an oscillation measurement signal representing such and containing a signal frequency corresponding to the wanted frequency, and to provide the oscillation measurement signal to the measuring device electronics, for example, namely a measuring—and operating circuit of the measuring device electronics formed by means of at least one microprocessor, for additional processing. In the case of measuring transducers of usually marketed vibronic density measuring devices, the oscillation sensors are most often likewise of electrodynamic type, consequently constructed in the manner of a solenoid. Accordingly, also the oscillation sensors of such a sensor arrangement are most often likewise formed respectively by means of a permanent magnet affixed on the measuring tube and at least one coil—, for example, affixed to the, in given cases present, other measuring tube or to the, in given cases present, counteroscillator—and permeated by a magnetic field of the permanent magnet. As a result of the oscillatory movements of the at least one measuring tube, the coil provides, at least at times, an induced measurement voltage.

Due to the wanted oscillations of the at least one measuring tube,—not least of all also for the case, in which the wanted oscillations of the at least one measuring tube are bending oscillations—, as is known, also Coriolis forces dependent on the instantaneous mass flow rate can be induced in the flowing medium. These can, in turn, bring about Coriolis oscillations dependent on the mass flow rate. The Coriolis oscillations superimpose on the wanted oscillations and have the wanted frequency. This occurs in such a manner that between inlet-side and outlet-side oscillatory movements of the at least one measuring tube performing wanted oscillations and at the same time flowed-through by the medium, a travel time—, respectively phase difference, can be detected, which is also dependent on the mass flow rate and, consequently, also usable as a measure for mass flow measurement. In the case of an at least sectionally curved measuring tube, in the case of which selected for the wanted oscillations is an oscillation form, in which the measuring tube is caused to move like a pendulum in the form of an end clamped cantilever, the resulting Coriolis oscillations correspond, for example, to that bending oscillation mode—, at times, also referenced as a twist-mode—, in which the measuring tube executes rotary oscillations about an imaginary rotary oscillation axis directed perpendicular to the imaginary oscillation axis, while, in contrast, in the case of a straight measuring tube, whose wanted oscillations are embodied as bending oscillations in a single imaginary plane of oscillation, the Coriolis oscillations are, for example, developed as bending oscillations essentially coplanar with the wanted oscillations. For the above already mentioned case, in which by means of the measuring device supplementally to density additionally also the mass flow rate of the respective medium guided in the measuring transducer should be ascertained, measuring transducers of the type being discussed have for the purpose of registering both inlet-side as well as also outlet-side oscillatory movements of the at least one measuring tube and for producing at least two electrical oscillation measurement signals influenced by the mass flow rate to be measured, furthermore, most often spaced from one another along the measuring tube, two or more oscillation sensors, which are so embodied and arranged that the oscillation measurement signals generated therewith and led to the measuring device electronics have not only, such as already mentioned, in each case, a wanted signal component, but that additionally also between the wanted signal components of the two oscillation measurement signals a travel time, respectively phase difference, dependent on the mass flow rate is measurable. Alternatively or supplementally to measuring also the mass flow rate supplementally to measuring the density, it is—such as already mentioned, respectively, among other things, shown in the above US-A 2011/0265580—additionally also possible, by means of such measuring transducers of vibration-type, consequently by means of therewith formed vibronic density measuring devices, supplementally also directly to measure a viscosity of the through flowing medium, for example, based on an electrical excitation power required for exciting, respectively maintaining, the wanted oscillations, respectively based on a damping of the wanted oscillations ascertained based on the excitation power, and to output such in the form of qualified viscosity measured values.

A coil applied in the case of a measuring transducer of the type being discussed—, for example, to form an oscillation exciter or an oscillation sensor—typically includes a coil support, for example, one of a synthetic material, such as a plastic, and/or a ceramic and/or a metal. The coil support has a straight passageway extending from a first end of the coil support formed by a first end face to a second end of the coil support distal to the first end and formed by a second end face, especially a second end face parallel to the first end face. Wound around the coil support is a coil wire of an electrically conductive material, for example, copper or platinum, respectively an alloy thereof, for example, a coil wire coated with an electrically insulating lacquer layer. The final mounting of such a coil is typically done using a screw positioned in the passageway of the coil support to attach the coil wire carrying coil support to the counteroscillator, respectively to the measuring tube, of the respective measuring transducer. Typically thereafter, consequently in the case of coil already located in the installed position, each of the two connecting line is electrically conductively connected, for example, namely manually soldered, to respective ends of the coil wire.

Due to the often very small distances between the individual already joined together assemblies of the measuring transducer to be manufactured, not least of all in the case of measuring transducers of lesser nominal diameter, respectively having comparatively small measuring tubes, a not insignificant measure of dexterity is necessary in the case of handling the connecting lines, respectively the operating means required for soldering, brazing, such as, for instance, a corresponding hand soldering device, respectively the corresponding solder material. This is coupled with a correspondingly increased risk, first of all, of producing unrecognized, defectively soldered connections. Moreover, there is in the case of soldering, brazing the connecting lines to the coil located in the installed position an increased risk of tearing the most often very thin coil wire, respectively damaging the equally only very thin insulation of the same, consequently of damaging or even destroying the coil.

SUMMARY

A object of the invention is, consequently, to provide a coil, in the case of which, on the one hand, the connecting of coil wire and connecting lines is simplified, and in the case of which, on the other hand, the risk of destroying the coil during or after connecting coil wire and connecting lines is lessened in comparison to conventional coils; this, especially, also in the case of application of the coil in a measuring transducer of vibration-type.

For achieving the object, the invention resides in a coil, for example, a coil for a measuring transducer of vibration-type, comprising:
  a platform, for example, a platform of a metal material and/or a circularly cylindrical and/or disk shaped platform, having a passageway, for example, a straight passageway and/or a passageway surrounded by a platform inner surface having an internal thread, namely a passageway extending from a first end of the platform formed by a first end face to a second end of the platform distal to the first end and formed by a second end face, for example, a second end face parallel to the first end face;
  a coil support, for example, a coil support of a synthetic material and/or a ceramic and/or a metal, namely a coil support having a passageway, for example a straight passageway, extending from a first end of the coil support formed by a first end face to a second end of the coil support distal to the first end and formed by a second end face, for example a second end face parallel to the first end face, wherein the coil support is so arranged relative to the platform,
    that the second end face of the coil support faces the platform and an intermediate space is formed between the second end face of the coil support and the first end face of the platform, and
    that the passageway of the coil support aligns with the passageway of the platform, for example, in such a manner that a screw is positionable extending both through the passageway of the coil support as well as also through the passageway of the platform;
  a screw accommodated both by the passageway of the coil support as well as also by the passageway of the platform, for example, namely a screw extending beyond the second end of the platform and/or embodied as a countersunk head screw, for the mechanical connecting of coil support and platform;
  a coil wire of an electrically conductive material wound around the coil support, for example, a metal coil wire, for example, namely a coil wire of copper or a copper alloy or platinum or a platinum alloy, and/or a coil wire coated with an electrically insulating lacquer layer;
  as well as at least two connecting lines, in each case, placed partially in the intermediate space formed between coil support and platform, for example, connecting lines affixed by means of a force interlocking effected within the intermediate space, of which connecting lines
    a first connecting line has at least one conductor of electrically conductive material, for example, a metal conductor and/or a conductor at least partially encased by a textile insulation, for example, namely a conductor of silver or a silver alloy or copper or a copper alloy, electrically conductively connected with a first end of the coil wire, and
    a second connecting line has at least one conductor of electrically conductive material, for example a metal conductor and/or a conductor at least partially encased by a textile insulation, for example, namely a conductor of silver or a silver alloy or copper or a copper alloy or of the same material as the conductor of the first connecting line, and the conductor of the second connecting line is electrically conductively connected with a second end of the coil wire.

Moreover, the invention resides also in a measuring transducer of vibration-type, comprising:
  at least one measuring tube, for example, an at least sectionally straight measuring tube and/or an at least sectionally curved measuring tube, wherein the measuring tube in either case has a lumen surrounded by a tube wall and is adapted to guide in the lumen a flowable medium, for example, a gas and/or a liquid, and concurrently to be caused to vibrate, for example, in such a manner that the metal tube executes mechanical oscillations about a static resting position associated therewith, which oscillations are suitable to induce in the flowing medium Coriolis forces dependent on a mass flow rate, and/or that the metal tube executes mechanical oscillations about a static resting position associated therewith, which oscillations are suitable to induce in the flowing medium frictional forces dependent on a viscosity of the medium, and/or that the metal tube executes mechanical oscillations about a static resting position associated therewith, which oscillations are suitable to induce in the flowing medium inertial forces dependent on a density of the medium;

a permanent magnet connected with the at least one measuring tube, for example, namely affixed outwardly on its tube wall;

as well as a coil as claimed in one of the preceding claims, wherein the coil is permeated by a magnetic field of the permanent magnet.

In a first embodiment of the coil of the invention, it is provided that the first end face of the platform has at least one cavity, for example, a cavity laterally spaced from its passageway and/or a groove shaped cavity, for accommodating at least one of the at least two connecting lines, for example, namely for accommodating both the first connecting line as well as also the second connecting line. Developing this embodiment of the invention further, it is, additionally, provided that the first end face of the platform has a first cavity, for example, a first cavity laterally spaced from its passageway and/or a groove shaped first cavity, for accommodating the first connecting line as well as a second cavity, for example, a second cavity laterally spaced from its passageway and/or groove shaped second cavity and/or a second cavity parallel to the first cavity, for accommodating the second connecting line; and that the first connecting line is partially accommodated by the first cavity and the second connecting line is partially accommodated by the second cavity.

In a second embodiment of the coil of the invention, it is provided that the second end face of the coil support has at least one cavity, for example, a cavity laterally spaced from its passageway and/or a groove shaped cavity, for accommodating at least one of the at least two connecting lines, for example, namely for accommodating both the first connecting line as well as also the second connecting line.

In a third embodiment of the coil of the invention, it is provided that coil support and platform are so arranged that the first end face of the platform and the second end face of the coil body face one another, for example, in such a manner that coil body and platform contact one another flushly.

In a fourth embodiment of the coil of the invention, it is provided that the coil support has a winding segment, for example, a hollow cylindrical winding segment, a first edge segment bordering on a first end of the winding segment, for example, a hollow cylindrical first edge segment and/or a first edge segment projecting to form an annular winding limiting surface, as well as a second edge segment bordering on a second end of the winding segment distal to the first end, for example, a second edge segment having a frustoconically shaped contour and/or a second edge segment projecting to form an annular winding limiting surface, and that the coil wire is namely wound on the winding segment. Developing this embodiment of the invention further, it is, additionally, provided that the passageway of the coil support has within the second edge segment a, for example, step shaped, cross-section change, for example, in such a manner that a bearing surface for a screw head of the screw is formed; and/or that the screw has a screw head and is so placed within the coil support that the screw head is positioned within the second edge segment.

In a fifth embodiment of the coil of the invention, it is provided that by means of the screw a screwed connection is formed, which transmits an axial clamping force to the coil support, namely a clamping force acting in the direction of an imaginary longitudinal axis of the screw, for example, in such a manner that coil support and/or screw have elastic deformations.

In a sixth embodiment of the coil of the invention, it is provided that platform and coil support together with the connecting lines are adapted to bring about in the intermediate space a force-based interlocking affixing the connecting lines, for example, with a frictional force dependent on a clamping force transmitted to the coil support by means of the screw.

In a seventh embodiment of the coil of the invention, it is provided that the coil wire is composed of copper or a copper alloy.

In an eighth embodiment of the coil of the invention, it is provided that the conductor of the first connecting line is composed of silver or a silver alloy.

In a ninth embodiment of the coil of the invention, it is provided that the conductor of the second connecting line is composed of the same material as the conductor of the first connecting line.

In a tenth embodiment of the coil of the invention, it is provided that the conductor of the first connecting line is encased at least partially by a textile insulation, for example, a fiberglass insulation.

In an eleventh embodiment of the coil of the invention, it is provided that the conductor of the second connecting line is at least partially encased by the same insulation as the conductor of the first connecting line.

In a twelfth embodiment of the coil of the invention, it is provided that the coil support is composed of a synthetic material, for example, a thermoplastic, synthetic material, for example, polyetheretherketone (PEEK).

In a thirteenth embodiment of the coil of the invention, it is provided that the conductor of the first connecting line is connected by material bonding with the first end of the coil wire.

In a fourteenth embodiment of the coil of the invention, it is provided that the conductor of the second connecting line is connected by material bonding with the second end of the coil wire.

In a further development of the coil of the invention, such further comprises a formed part, for example, a formed part of a synthetic material and/or a ceramic and/or a metal and/or of the same material as the coil support, wherein the formed part has a passageway, for example, a straight passageway, extending from a first end of the formed part formed by a first end face to a second end of the formed part distal to the first end and formed by a second end face, for example, a second end face parallel to the first end face. Further in the case of this further development of the invention, it is provided that the formed part is placed in the intermediate space formed between coil support and platform and so arranged relative to coil support and platform that the passageway of the formed part aligns both with the passageway of the platform as well as also with the passageway of the coil support, for example, in such a manner that a screw can be extended through the aligned passageways; and the screw is partially accommodated also by the passageway of the formed part.

In a first embodiment of this further development of the coil of the invention, it is provided that the formed part is so arranged relative to coil support and platform that the first end face of the formed part faces the coil support and the second end face of the formed part faces the platform, for example, in such a manner that formed part and platform contact one another flushly and/or that formed part and coil support contact one another flushly.

In a second embodiment of this further development of the coil of the invention, it is provided that the first end face of the formed part has at least one cavity, for example, a cavity spaced laterally from its passageway and/or a groove shaped cavity, for accommodating at least one of the at least two connecting lines, for example, namely for accommodating both the first connecting line as well as also the second connecting line.

In a third embodiment of this further development of the coil of the invention, it is provided that the first end face of the formed part has a first cavity, for example, a first cavity spaced laterally from its passageway and/or a groove shaped first cavity, for accommodating the first connecting line, as well as a second cavity, for example, a second cavity spaced laterally from its passageway and/or a groove shaped second cavity and/or a second cavity parallel to the first cavity, for accommodating the second connecting line; and that the first connecting line is partially accommodated by the first cavity and the second connecting line is partially accommodated by the second cavity.

A basic idea of the invention is to increase the mechanical strength of the total coil, including the connecting lines connected with the coil wire, by securing the connecting lines directly to the coil support, along with a corresponding affixing also of the ends of the coil wire wound on the coil support and connected with the connecting lines. The coil can, thus, in advantageous manner also be embodied as a prefabricated assembly, namely an assembly ready for assembly with additional assemblies, for example, also additional assemblies of a measuring transducer of vibration-type, without a significant risk of a subsequent damaging of the coil, for instance, from breaking the connecting lines, respectively the coil wire, in the case of transport or in the case of installation of the coil. This has, among other things, also the advantage that the rather complex conventional connecting of coil wire and connecting lines in the installed position of the respective coil in the case of the manufacture of measuring transducers of vibration-type can be avoided by performing the connecting of coil wire and connecting lines outside the installed position, respectively remotely from the respective measuring tube, consequently at a freely accessible workplace.

The invention as well as other advantageous embodiments thereof will now be explained in greater detail based on examples of embodiments, which are shown in the figures of the drawing. Equal parts are provided in all figures with equal reference characters; when perspicuity requires or it otherwise appears sensible, already used reference characters are omitted in subsequent figures. Other advantageous embodiments or further developments, especially also combinations of, first of all, only individually explained aspects of the invention, will become evident, furthermore, from the figures of the drawing, as well as also the dependent claims per se. The figures of the drawing show as follows:

DETAILED DESCRIPTION IN CONJUNCTION WITH THE DRAWINGS

Figure 1:
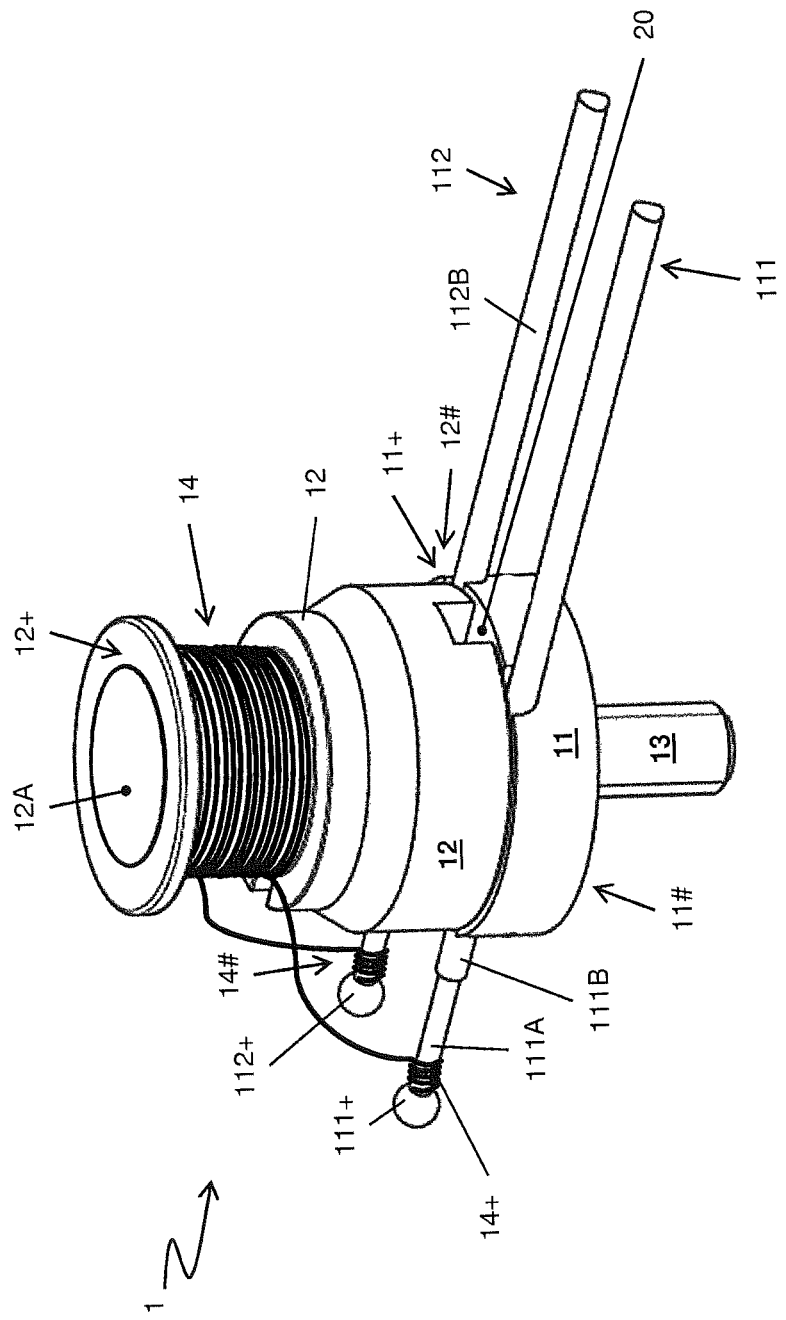
FIGS. 1, 2, 3 in different, partially exploded, views, an example of a embodiment of a coil of the invention, for example, one useful as a component of a measuring transducer of vibration-type, respectively a vibronic measuring device formed therewith.
Figure 2:
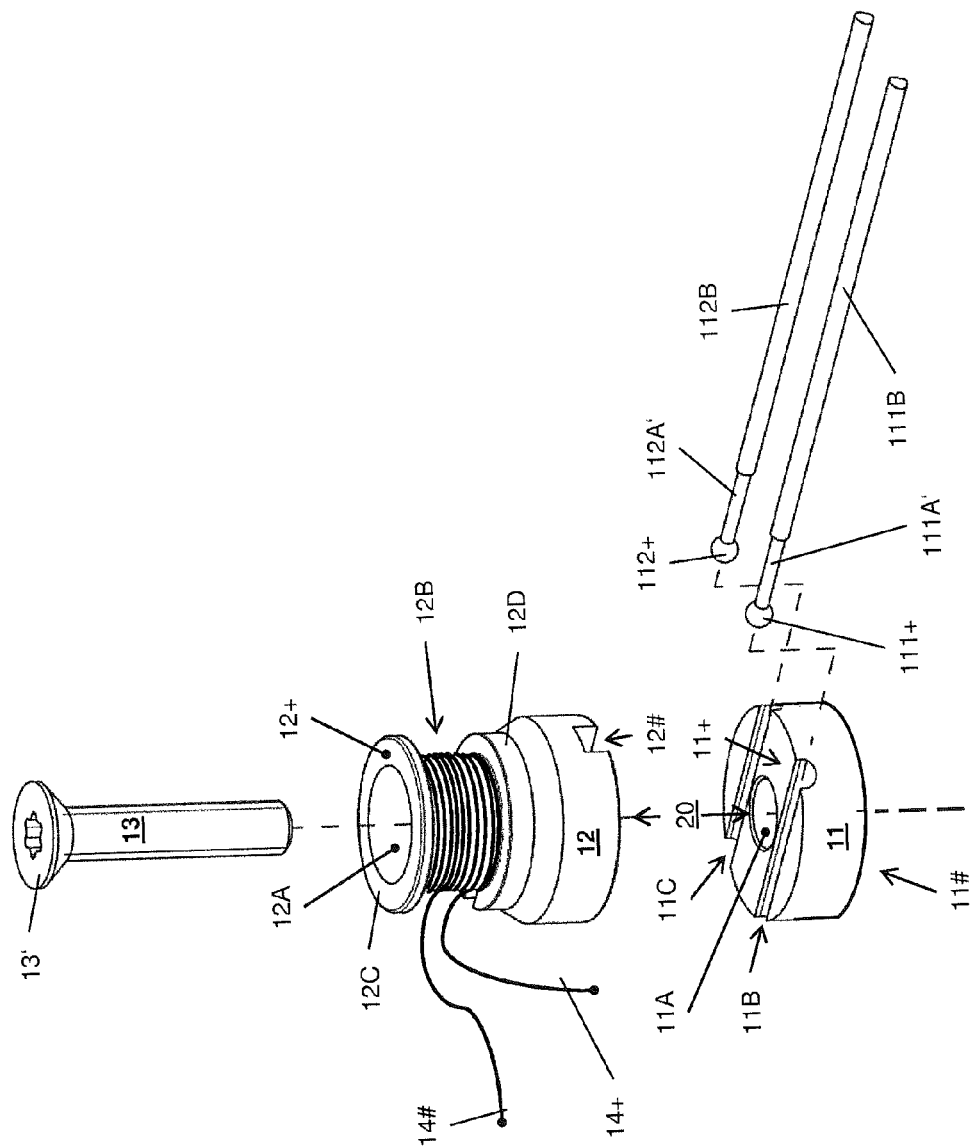
Figure 3:
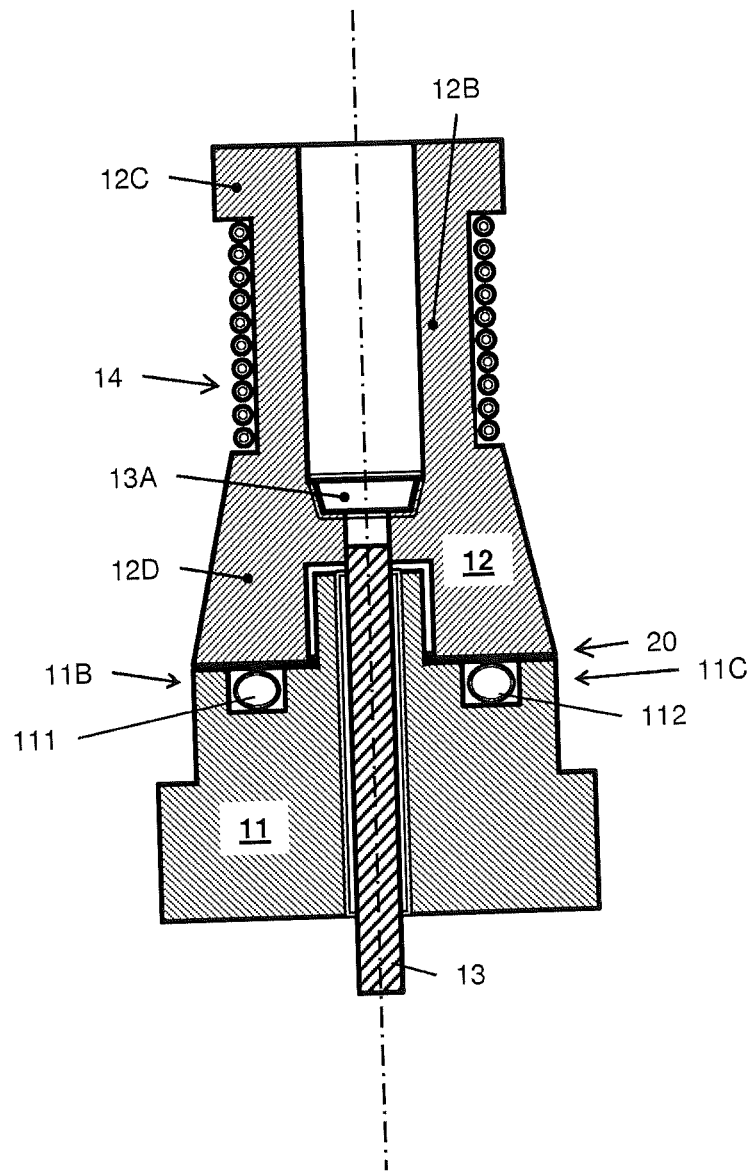

Shown in FIGS. 1, 2 and 3 is an example of an embodiment of a coil 1 of the invention, for example, one useful as a component of a measuring transducer of vibration-type, respectively a vibronic measuring device formed therewith.

Coil 1 comprises a platform 11 having a first end 11+ formed by a first end face and a second end 11# distal to the end 11+ and formed by a second end face, for example, one parallel to the first end face, a coil support 12 having a first end 12+ formed by a first end face and a second end 12# distal to the end 12+ and formed by a second end face, for example, one parallel to the first end face, as well as a coil wire 14 of an electrically conductive material, for example, namely copper or a copper alloy or platinum or a platinum alloy wound around the coil support. The platform 11—here embodied to be circularly cylindrical shaped, respectively disc shaped—can, for example, be produced from a metal material, for example, steel or titanium, respectively a titanium alloy. Equally for example, also the coil support can be of a metal, for example, namely steel, titanium, respectively a titanium alloy or also the same metal as the platform 11. The material for the coil support 12 can, moreover, however, also be a ceramic, as well as also synthetic material, such as plastic, for example, also a thermoplastic synthetic material, for example, namely polyetheretherketone (PEEK). The coil wire 14 can, in turn, be jacketed by an electrically insulating lacquer layer and/or embedded in an electrically insulating material, for example, a synthetic material or plastic, which jackets windings formed by means of the coil wire on the coil support. Particularly for the case, in which the coil wire 14, as shown schematically in FIG. 2, is wound as only one ply on the coil support, an option is, as well as also provided in the above mentioned US-A 2006/0081069, to form in the coil support also an external thread for accommodating the coil wire and to insert the coil wire into the groove of the external thread. Alternatively or supplementally, the coil wire 14 wound on the coil support 12 can be coated with a protective layer of an electrically poorly or non conducting material, for example, a synthetic material, a glass or an enamel.

In the case of the coil of the invention, platform and coil support are adapted to be mechanically connected with one another, for example, also releasably, by means of a screw 13. For such purpose, the platform 11 has a passageway 11A, for example a straight, respectively circularly cylindrical, passageway 11A extending from its end 11+ to its end 11# and the coil support 12 has a passageway 12A extending from its end 12+ to its end 12#, for example, a straight, respectively only sectionally circularly cylindrical, passageway. Furthermore, the coil support 12 is so arranged relative to the platform 11 that the second end face of the coil support facing the platform 11—here namely, for example, the first end face of the platform 11—and the passageway 12A of the coil support 12 align with the passageway 11A of the platform, and, indeed, in such a manner that, such as directly evident from the combination of FIGS. 1, 2 and 3, the screw 13—, for example, embodied as a countersunk head screw— is so positionable therein that it is partially accommodated by the passageway 11A, as well as also partially by the passageway 12A. In order to enable a screwing together of the coil 1 with additional add-on parts, respectively to enable a simple connection opportunity for the coil 1, the screw 13 according to a embodiment of the invention is, matched to the particular size of the two traversing openings 11A, 12A, so dimensioned that it extends beyond the second end of the platform, after it is positioned in the two traversing openings 11A, 12A. Serving for forming a screwed connection affixing platform 11 and coil support 12 to one another can be, for example, a nut pressing against the platform 11; the screwed connection can, however, for example, also be produced, as schematically indicated in FIG. 3, by providing the inner surface of the platform 11 surrounding the passageway 11A of the platform 11 with an internal thread, which engages with a corresponding external thread of the screw 13.

As evident from FIGS. 1, 2, respectively 3, for electrical connecting with an electronic circuit—(not shown)—spatially remote therefrom, for example, namely an electronics of a vibronic measuring device, or with another electrical component, the coil 1 includes, furthermore, a first connecting line 111 with at least one conductor 111A of an electrically conductive material as well as at least a second connecting line 112 with at least one conductor 112A of an electrically conductive material. The conductors of the connecting lines 111, 112 can, for example, be of the same material, respectively, for example, in each case, of silver or a silver alloy or copper or a copper alloy. Each of the connecting lines 111, 112 includes—, as well as also directly evident from a combination of FIGS. 1 and 2—additionally an insulation 111", respectively 112", for example, tubular insulation, of an electrically non or poorly conducting material jacketing the particular conductor 111', respectively 112'. Particularly for the mentioned case, in which the coil 1 serves, consequently is provided, as a component of a measuring transducer of vibration-type involving exposure to mechanical oscillations during operation, the connecting lines 111, 112 have, according to an additional embodiment, for the electrical insulation of the conductors, in each case, a textile insulation manufactured, for example, by means of glass fibers. Alternatively thereto or in supplementation thereof, the insulation can, however, for example, also be formed by means of a homogeneous lacquer layer or a plastic shell surrounding the particular conductors. As shown schematically in FIG. 1, the conductor of the connecting line 111 is electrically conductingly connected, for example, namely by material bonding, respectively by means of a soft—or a hard solder connection, with an exposed, namely not covered by insulation, first end 14+ of the coil wire 14 and the conductor of the connecting line 112 with an, equally as the first end 14+, not covered by insulation, second end 14+ of the coil wire.

In the case of the coil 1 of the invention, the intermediate space 20 resulting between the second end face of the coil support and the first end face of the platform 11 is utilized, especially, supplementally, to affix the connecting lines 111, 112 in such a manner that a strain relief for connecting lines 111, 112 is provided for protecting the above mentioned connections (namely those made between the conductor of the connecting line 111 and the end 14+ of the coil wire, respectively the conductor of the connecting line 112 and the end 14# of the coil wire) between the connecting lines 111, 112 and the coil wire 14, respectively also the coil wire 14 per se, against possible overloadings, for instance, as a result of tensile—or also shaking forces acting on the connecting lines, respectively a destruction associated therewith. For such purpose, in the case of the coil of the invention, each of the at least two connecting lines 111, 112 is, in installed position, in each case, placed partially in the intermediate space 20 formed between coil support and platform, in order to be affixed by means of a force interlocking formed there by the interaction of platform, coil support and screw. In the example of an embodiment shown here, a screwed connection is formed by means of the screw 13, which transmits an axial clamping force onto the coil support, namely a force acting in the direction of an imaginary longitudinal axis of the screw; this, especially, in such a manner that coil support and/or screw experience elastic deformations. Platform 11 and coil support 12 together with the connecting lines 111, 112 are, furthermore, adapted to bring about in the intermediate space 20 by making use of return—, respectively clamping, forces generated by elastic deformations of the coil support, respectively the screw, a force-based interlocking affixing the connecting lines. The magnitude of the clamping forces, respectively the frictional force resulting therefrom, affixing the connecting lines can be correspondingly set by means of the screw, respectively by a tightening torque applied for its securement.

Particularly in the case of application of connecting lines with textile insulation for the respective conductors, it is, furthermore, provided to extend the insulation at least into the intermediate space 20, ideally, however,—such as indicated in FIG. 1—also slightly, more, in such a manner that sections 111', 112' of each of the conductors within the intermediate space 20 are encased by the respectively associated insulation 111", 112". In this way, on the one hand, very high holding forces can be achieved for the force-based interlocking affixing the connecting lines 111, 112 and, on the other hand, in very simple, equally as well effective, manner a splicing or tearing of the insulation is prevented, at least, however, a further propagation of possible tears in the insulation safely suppressed.

Figure 4:
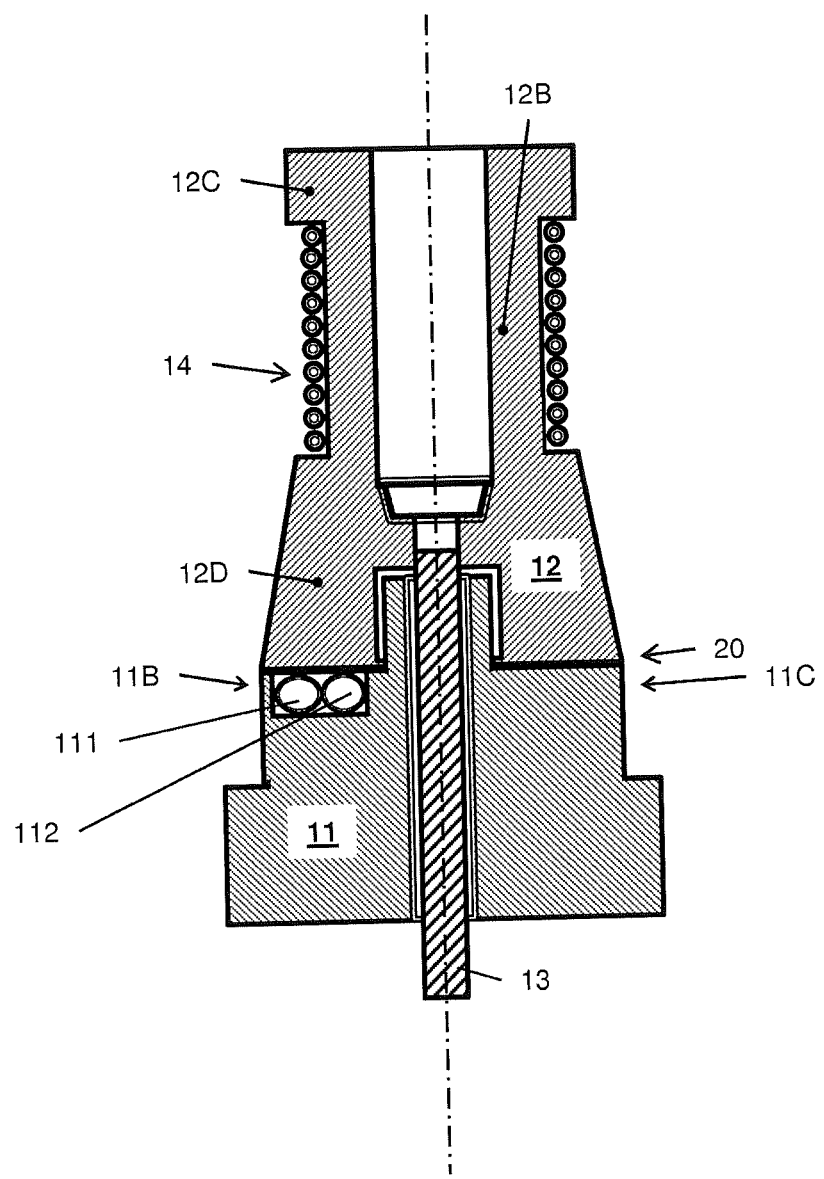
FIGS. 4, 5, 6 in sectioned side views, embodiments of a coil of the invention.
Figure 5:
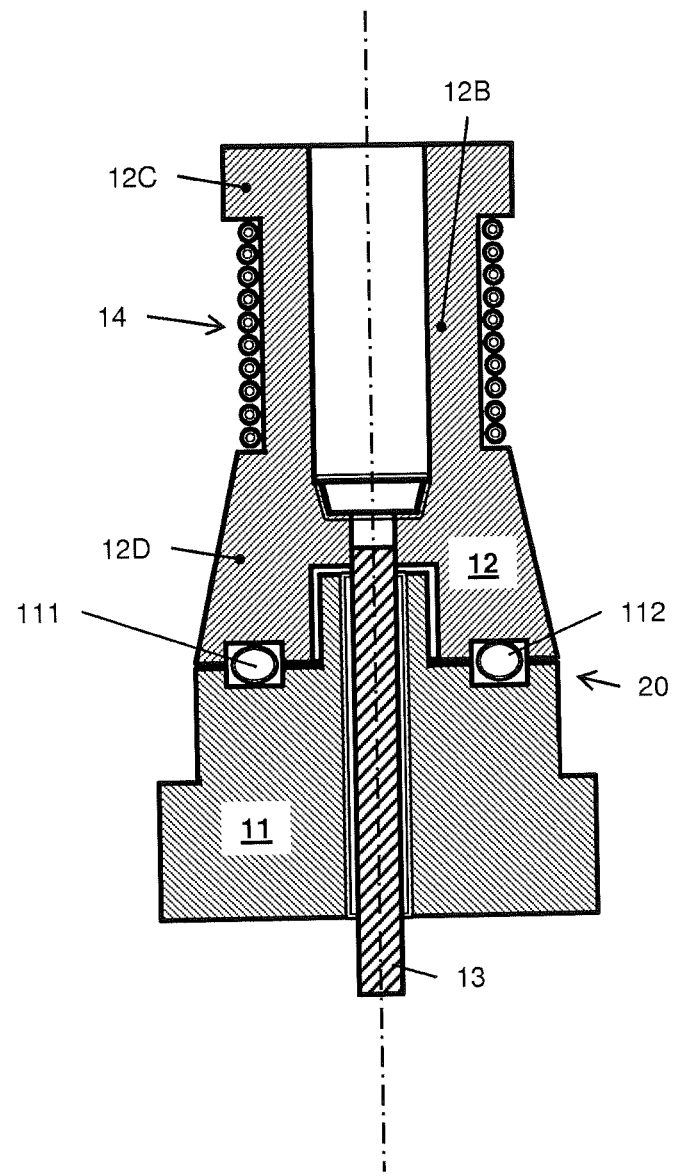

For the purpose of improving a lateral holding of the subsections of the connecting lines 111, 112 positioned within the intermediate space 20, according to an additional embodiment of the invention, at least one cavity 11B, for example, a groove shaped cavity 11B spaced laterally from its passageway 11A is provided in the first end face of the platform 11 for accommodating at least one of the at least two connecting lines 111, 112, respectively a subsection thereof. Said cavity 11B can, as well as also shown schematically in FIG. 4, be adapted to accommodate both the connecting line 111 as well as also the connecting line 112, respectively subsections thereof. It can, however, also be quite advantageous, supplementally to cavity 11B, to form another, second cavity 11C, for example, a likewise groove shaped cavity 11C, respectively a cavity 11C constructed equally to the cavity 11B—into the second end face of the platform 11, for example, in such a manner that the two cavities 11B, 11C—here essentially parallel to one another, respectively essentially straight—are spaced from one another, and, equally as well, each of the two cavities 11B, 11C extends laterally separated from the passageway 11A. In another embodiment of the invention, consequently, the first end face of the platform 11 includes both a cavity 11B, for example, a groove shaped cavity 11B, laterally spaced from the passageway 11A for accommodating the connecting line 111 as well as a second cavity 11C, for example, a groove shaped cavity 11C and/or a cavity 11C spaced parallel to the first cavity and laterally from the passageway 11A, for accommodating the connecting line 112, and it is additionally provided that the connecting line 111 is accommodated partially by the cavity 12B and the connecting line 112 partially by the cavity 12C. Alternatively or supplementally, however, the coil body, as well as also shown schematically in FIG. 5, can also have one or more such cavities for accommodating the connecting line 111, respectively 112. For example, coil support and platform can also be so arranged that the first end face of the platform and the second end face of the coil body are not only facing one another, but, additionally, coil body and platform also contact one another flushly. Moreover, the cavity can, for example, also have cross grooves, respectively scores, providing a shape-based interlocking with the respectively associated connecting line, consequently increasing the holding—, respectively pullout, forces established in the installed position.

For simplifying the mounting of the coil 1, not least of all also for the positioning of the connecting lines, however, also for the purpose of increasing the holding forces achieved by the force-based interlocking, the coil 1 according to an additional embodiment of the invention includes a formed part 15 having a first end 15+ formed by a first end face and a second end 15# distal to the first end 15+ and formed by a second end face, for example, a second end face parallel to the first end face. In the example of an embodiment shown here, the formed part 15, for example, a formed part 15 of a synthetic material and/or a ceramic and/or a metal and/or of the same material as the coil support, is so arranged relative to coil support 12 and platform 11 that the first end face of the formed part faces the coil support and the second end face of the formed part faces the platform. Furthermore, the formed part and platform are so embodied that they contact one another as flushly as possible in the installed position.

Figure 6:
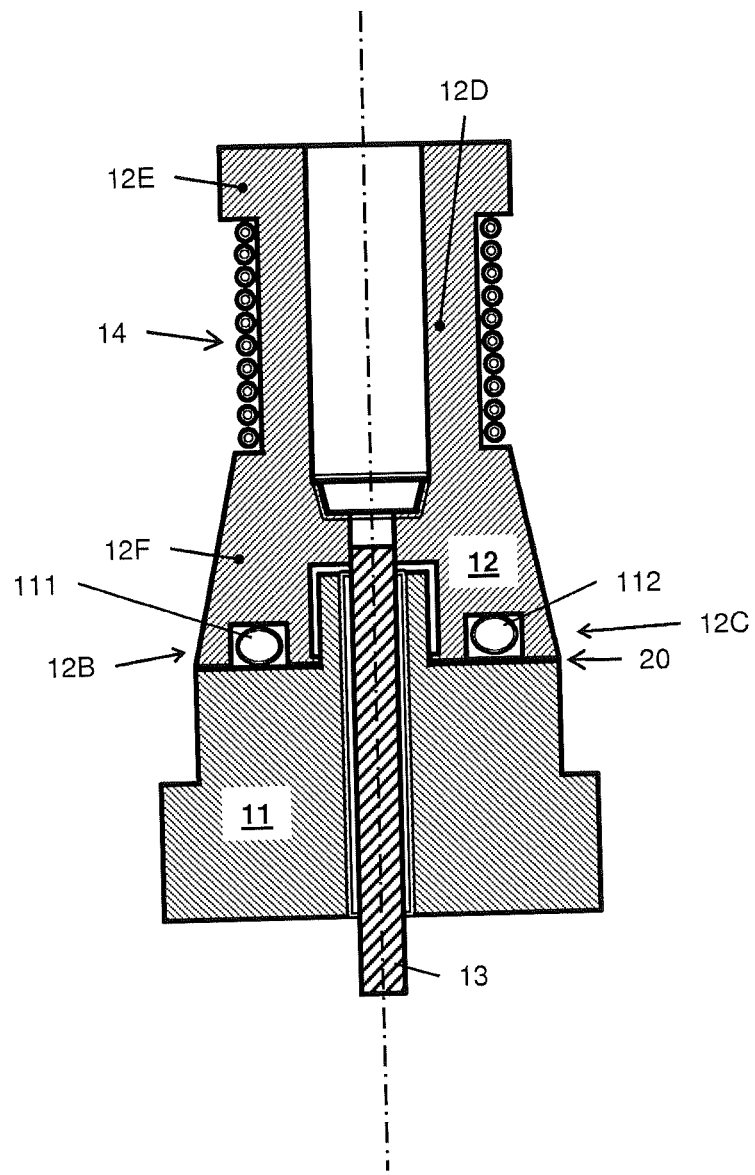
Figure 7:
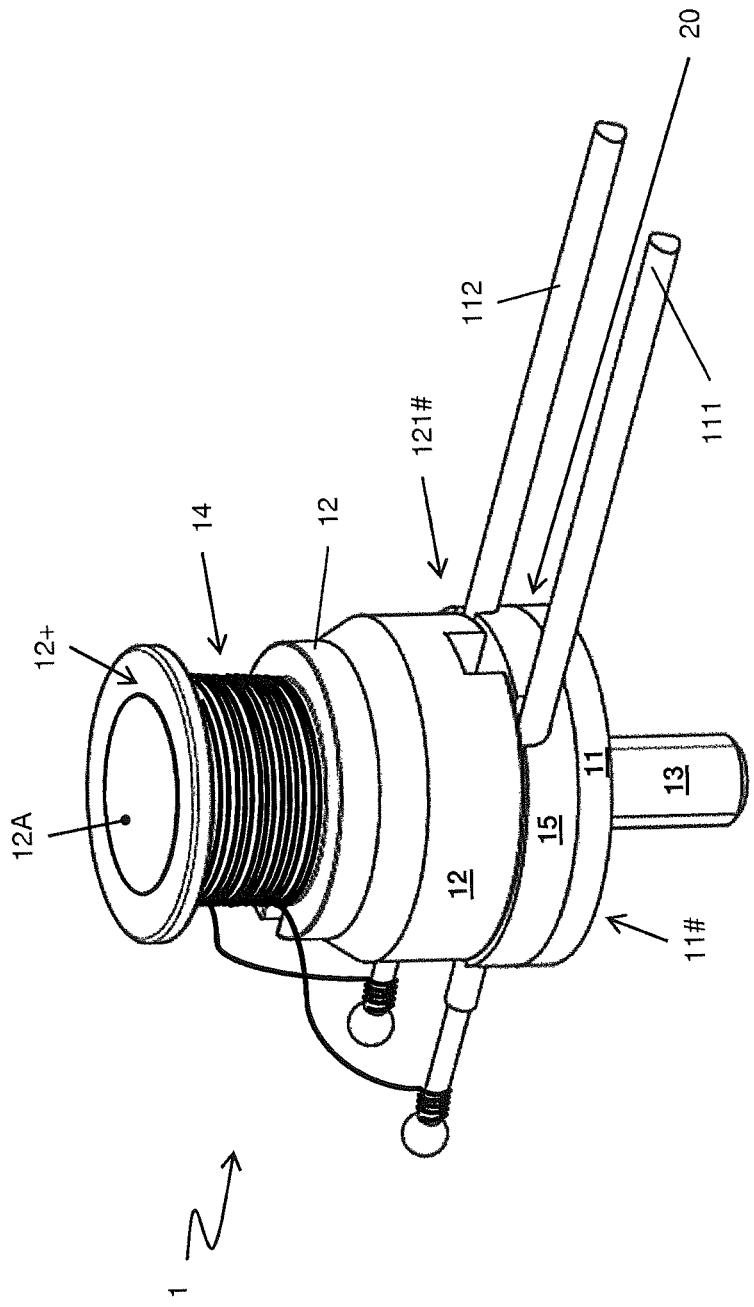
FIG. 7, 8, 9 in different, partially exploded, views, a further example of a embodiment of a coil of the invention, for example, one useful as a component of a measuring transducer of vibration-type, respectively a vibronic measuring device formed therewith.
Figure 8:
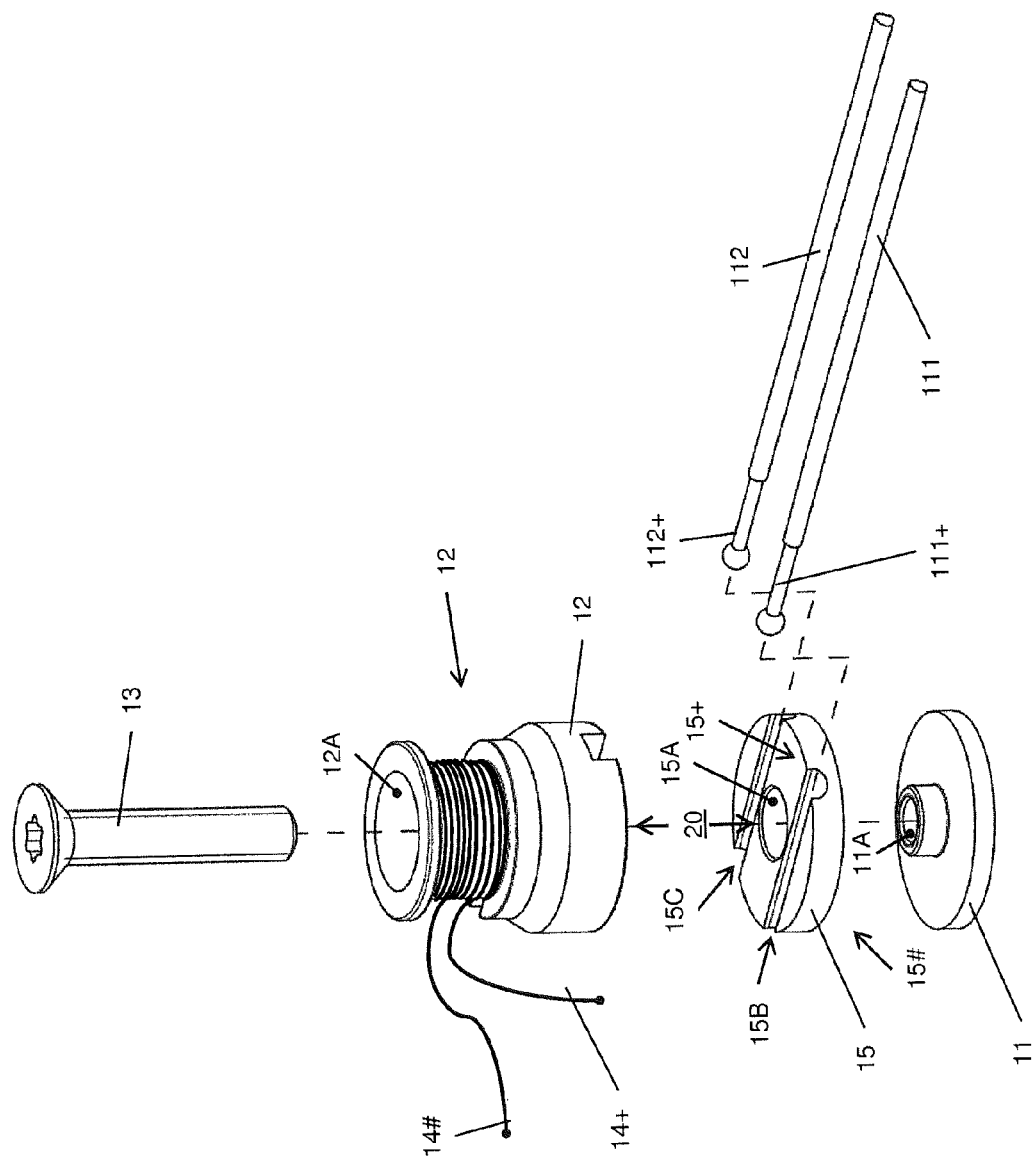
Figure 9:
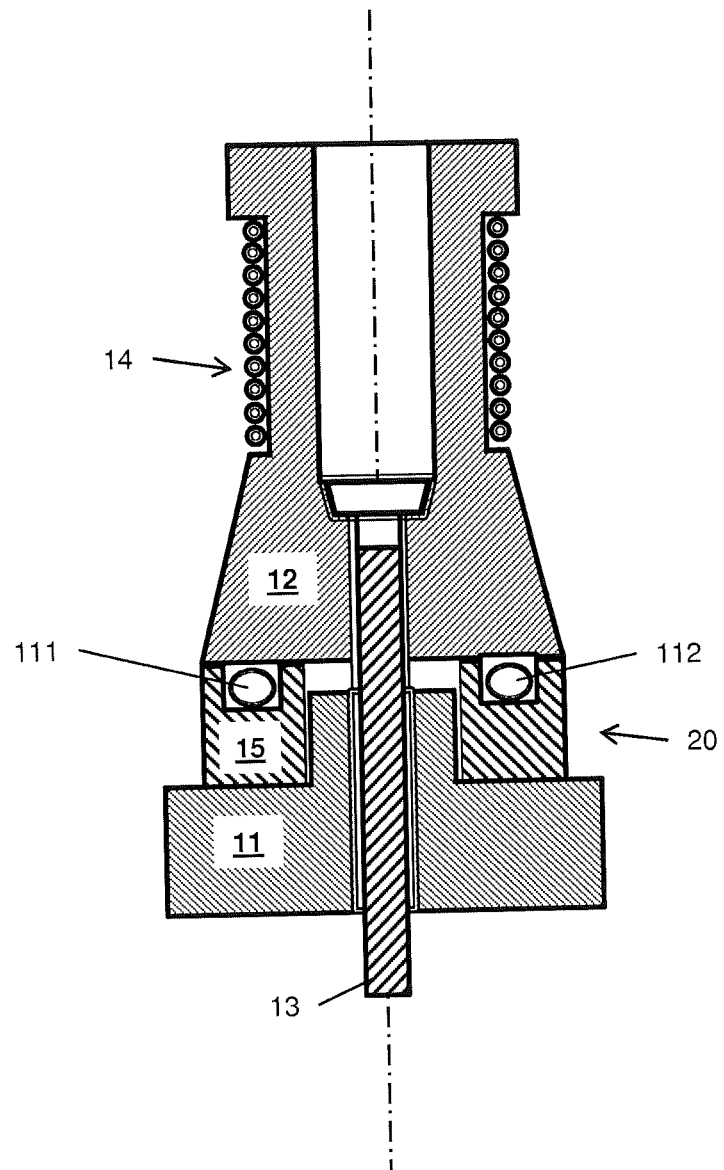

The formed part 15 additionally includes a passageway 15A, for example, a straight and/or circularly cylindrical passageway 15A extending from the end 15+ to the end 15#, and is placed in the installed position in the intermediate space 20 formed between coil support and platform. The formed part 15 is, in such case, so arranged relative to coil support and platform that the passageway 15A—such as directly evident from a combination of FIGS. 6, 7 and 8—aligns both with the passageway 11A of the platform 11 as well as also with the passageway 12A of the coil support 12, namely likewise so that, such as directly evident from the combination of FIGS. 6, 7 and 8, the screw 13 can pass at the same time through the passageway 11A, the passageway 12A, as well as also the passageway 15A, consequently is accommodated partially by the passageway 11A, the passageway 12A, as well as also the passageway 15A. Moreover, the formed part 15, such as evident from the combination of FIGS. 7 and 8 and 9, can also have one or more groove shaped cavities spaced laterally from its passageway 15A for accommodating one or more connecting lines of the coil. Therefore, according to an additional embodiment of the invention, formed in the first end face of the formed part 15 is at least one cavity 15B for accommodating at least one of the at least two connecting lines 111, 112, for example, also for accommodating both the connecting line 111 as well as also the connecting line 112. Moreover, the formed part 15 can, however, also have at least one other cavity 15C, for example, a cavity 150 also parallel to cavity 15B, respectively of equal construction, so that, as well as also shown in FIGS. 7 and 8 and 9, the connecting line 111 is accommodated partially by the cavity 15B and the connecting line 112 partially by the cavity 15C. The at least one cavity, respectively the cavities, and the connecting lines 111, 112 can in advantageous manner, furthermore, be so dimensioned, matched to one another, that, as a result, the formed part and coil support, such as evident from FIG. 7, respectively 9, contact one another flushly in the installed position.

Figure 10:
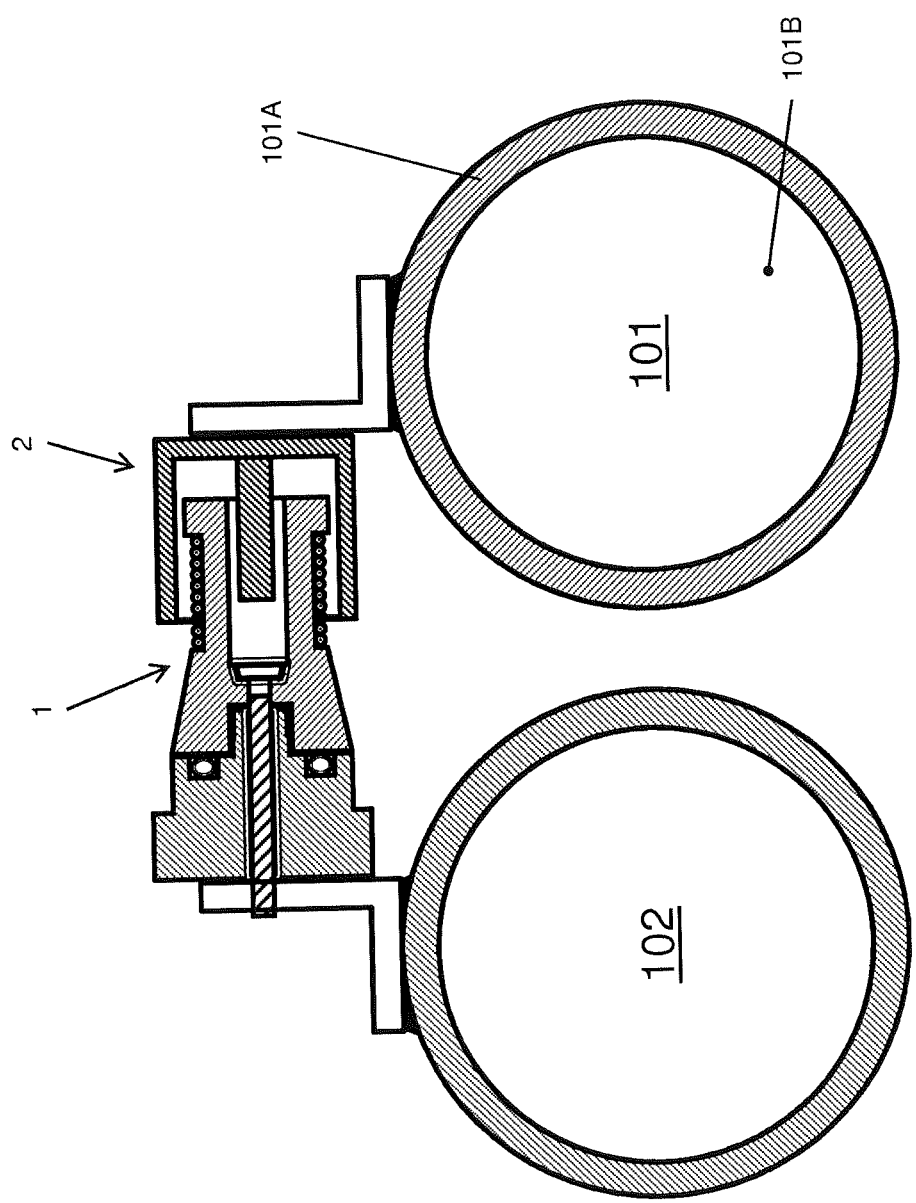
FIG. 10 in a sectioned side view, a measuring tube of a measuring transducer of vibration-type with a permanent magnet secured thereto and a coil of the invention interacting with the permanent magnet.

As already mentioned, the coil of the invention is, especially, also provided to serve as a component of a measuring transducer of vibration-type, for example, namely as an oscillation exciter or as an oscillation sensor thereof, respectively as a vibronic measuring device formed by means of such a measuring transducer, for example, a Coriolis mass flow measuring device, a density measuring device or a viscosity measuring device. Such a measuring transducer includes, such as shown schematically in FIG. 10, at least one measuring tube 101 having a lumen 101B surrounded by a tube wall 101A. The at least one measuring tube, for example, an at least sectionally straight and/or at least sectionally curved, measuring tube is especially adapted to guide in its lumen 101B a flowable medium, respectively a medium flowing at least at times, for example, a gas or a liquid, and concurrently to be caused to vibrate, for example, such that the at least one measuring tube can execute mechanical oscillations about a static resting position associated therewith, mechanical oscillations which are suitable to induce in the flowing medium Coriolis forces dependent on a mass flow rate, m, and/or which are suitable to induce in the flowing medium frictional forces dependent on a viscosity, $\eta$, of the medium, and/or which are suitable to induce in the flowing medium inertial forces dependent on a density, $\rho$, of the medium. The measuring transducer includes, furthermore, a permanent magnet 2 connected with the at least one measuring tube 101—here namely a permanent magnet 2 affixed outwardly on its tube wall 101A, for example, a tube wall of a stainless steel, titanium, tantalum, zirconium or a nickel based alloy. The coil 1 is, in turn, so placed, that it is permeated by a magnetic field of the permanent magnet. For example, the coil 1 can, such as indicated in FIG. 10, be secured on an additional measuring tube, in given cases, also an additional measuring tube constructed equally to measuring tube 101—, or, however, also—such as in the case of measuring transducers of vibration-type with a single measuring tube quite usual—on an, in given cases, present counteroscillator, operationally not flowed through by a medium to be measured.

The invention claimed is:
1. A coil, comprising:
a platform including a passageway, namely a passageway extending from a first end of the platform formed by a first end face to a second end of the platform distal to the first end and formed by a second end face;
a coil support, namely a coil support including a passageway extending from a first end of the coil support formed by a first end face to a second end of the coil support distal to the first end and formed by a second end face, wherein the coil support is so arranged relative to the platform that the second end face of the coil support faces the platform and an intermediate space is formed between the second end face of the coil support and the first end face of the platform and that the passageway of the coil support aligns with the passageway of the platform;

a screw accommodated both by the passageway of the coil support as well as also by the passageway of the platform for the mechanical connecting of coil support and platform;

a coil wire of an electrically conductive material wound around the coil support; and as well as at least two connecting lines, in each case, placed partially in the intermediate space formed between coil support and platform, of which connecting lines a first connecting line includes at least one conductor of electrically conductive material electrically conductively connected with a first end of the coil wire and a second connecting line includes at least one conductor of electrically conductive material electrically conductively connected with a second end of the coil wire.

2. The coil as claimed in claim 1, wherein:
the first end face of the platform exhibits at least one cavity for accommodating at least one of the at least two connecting lines.

3. The coil as claimed in claim 2, wherein:
the first end face of the platform exhibits a first cavity for accommodating the first connecting line as well as a second cavity for accommodating the second connecting line; and
the first connecting line is partially accommodated by the first cavity and the second connecting line is partially accommodated by the second cavity.

4. The coil as claimed in claim 1, wherein:
the second end face of the coil support exhibits at least one cavity for accommodating at least one of the at least two connecting lines.

5. The coil as claimed in claim 1, wherein:
said coil support and platform are so arranged that the first end face of the platform and the second end face of the coil body face one another.

6. The coil as claimed in claim 1, further comprising:
a formed part, wherein the formed part includes a passageway extending from a first end of the formed part formed by a first end face to a second end of the formed part distal to the first end and formed by a second end face,
wherein:
the formed part is placed in the intermediate space formed between coil support and platform and so arranged relative to coil support and platform that the passageway of the formed part aligns both with the passageway of the platform as well as also with the passageway of the coil support; and
the screw is partially accommodated also by the passageway of the formed part.

7. The coil as claimed in claim 6, wherein:
the formed part is so arranged relative to coil support and platform that the first end face of the formed part faces the coil support and the second end face of the formed part faces the platform.

8. The coil as claimed in claim 6, wherein:
the first end face of the formed part exhibits at least one cavity for accommodating at least one of the at least two connecting lines.

9. The coil as claimed in claim 6, wherein:
the first end face of the formed part exhibits a first cavity for accommodating the first connecting line as well as a second cavity for accommodating the second connecting line; and the first connecting line is partially accommodated by the first cavity and the second connecting line is partially accommodated by the second cavity.

10. The coil as claimed in claim 1, wherein:
the coil support includes a winding segment, a first edge segment bordering on a first end of the winding segment, as well as a second edge segment bordering on a second end of the winding segment distal to the first end, and
the coil wire is namely wound on the winding segment.

11. The coil as claimed in claim 10, wherein:
the passageway of the coil support exhibits within the second edge segment an cross-section change.

12. The coil as claimed in claim 1, wherein:
by means of the screw a screwed connection is formed, which transmits an axial clamping force onto the coil support, namely a clamping force acting in the direction of an imaginary longitudinal axis of the screw.

13. The coil as claimed in claim 1, wherein:
said platform and coil support together with the connecting lines are adapted to bring about in the intermediate space a force-based interlocking affixing the connecting lines.

14. Coil as claimed in claim 12, wherein:
the force-based interlocking shows a frictional force dependent on the clamping force.

15. The coil as claimed in claim 1, wherein:
the coil wire is composed of copper or a copper alloy.

16. A measuring transducer of vibration-type, comprising:
at least one measuring tube, wherein the measuring tube in either case includes a lumen surrounded by a tube wall and is adapted to guide in the lumen a flowable medium and concurrently to be caused to vibrate;
a permanent magnet connected with the at least one measuring tube;
and a coil as claimed in claim 1, wherein:
the coil is permeated by a magnetic field of the permanent magnet.

17. The coil as claimed in claim 1, wherein:
the platform is of a metal material.

18. The coil as claimed in claim 1, wherein:
the platform is circularly cylindrical shaped.

19. The coil as claimed in claim 1, wherein:
the platform is circularly disk shaped.

20. The coil as claimed in claim 1, wherein:
the passageway is straight.

21. The coil as claimed in claim 1, wherein:
the passageway is surrounded by a platform inner surface exhibiting an internal thread.

22. The coil as claimed in claim 1, wherein:
the second end face of the platform is parallel to the first end face of the platform.

23. The coil as claimed in claim 1, wherein:
the coil support is of a synthetic material.

24. The coil as claimed in claim 1, wherein:
the coil support is of ceramic.

25. The coil as claimed in claim 1, wherein:
the coil support is of a metal.

26. The coil as claimed in claim 1, wherein:
the passageway of the coil support is straight.

27. The coil as claimed in claim 1, wherein:
the second end face of the coil support is parallel to the first end face of the platform.

28. The coil as claimed in claim 1, wherein:
the screw extends beyond the second end of the platform.

29. The coil as claimed in claim 1, wherein:
the screw is embodied as a countersunk head screw.

30. The coil as claimed in claim 1, wherein:
the coil wire is metal.

31. The coil as claimed in claim 1, wherein:
the coil wire is of platinum or platinum alloy.

32. The coil as claimed in claim 1, wherein:
the coil wire is coated with an electrically insulating lacquer layer.

33. The coil as claimed in claim 1, wherein:
the connecting lines are affixed by means of a force interlocking effected within the intermediate space.

34. The coil as claimed in claim 1, wherein:
the at least one conductor of the first connecting line is a metal conductor.

35. The coil as claimed in claim 1, wherein:
the at least one conductor of the first connecting line is a conductor of silver or silver alloy.

36. The coil as claimed in claim 1, wherein:
the at least one conductor of the second connecting line is a conductor of silver or silver alloy.

37. The coil as claimed in claim 1, wherein:
the at least one conductor of the first connecting line is at least partially encased by a textile insulation.

38. The coil as claimed in claim 1, wherein:
the at least one conductor of the second connecting line is at least partially encased by the same insulation as the conductor of the first connecting line.

39. The coil as claimed in claim 1, wherein:
the at least one conductor of the second connecting line is at least partially encased by a textile insulation.

40. The coil as claimed in claim 1, wherein:
the at least one conductor of the second connecting line is of the same material as the conductor of the first connecting line.

41. The coil as claimed in claim 2, wherein:
the at least one cavity of the first end face of the platform is spaced laterally from passageway of the platform.

42. The coil as claimed in claim 2, wherein:
the at least one cavity of the first end face of the platform is groove shaped.

43. The coil as claimed in claim 2, wherein:
the at least one cavity of the first end face of the platform is adapted to accommodate both the first connecting line as well as also the second connecting line.

44. The coil as claimed in claim 4, wherein:
the at least one cavity of the second end face of the coil support is spaced laterally from passageway of the coil support.

45. The coil as claimed in claim 4, wherein:
the at least one cavity of the second end face of the coil support is groove shaped.

46. The coil as claimed in claim 4, wherein:
the at least one cavity of the second end face of the coil support adapted to accommodate both the first connecting line as well as also the second connecting line.

47. The coil as claimed in claim 1, wherein:
said platform and coil support together with the connecting lines are adapted to bring about in the intermediate space a force-based interlocking affixing the connecting lines with a frictional force dependent on a clamping force transmitted to the coil support by means of the screw.

48. The coil as claimed in claim 1, wherein:
the coil support is composed of a synthetic material.

49. The coil as claimed in claim 1, wherein:
the coil support is composed of polyetheretherketone (PEEK).

50. The coil as claimed in claim 1, wherein:
the conductor of the first connecting line is connected by material bonding with the first end of the coil wire.

51. The coil as claimed in claim 1, wherein:
the conductor of the second connecting line is connected by material bonding with the second end of the coil wire.

* * * * *